United States Patent
Georges et al.

(10) Patent No.: US 12,171,849 B2
(45) Date of Patent: Dec. 24, 2024

(54) SUNSCREEN EMULSION COMPRISING SILICONE EMULSIFIER BLEND

(71) Applicant: L'OREAL, Paris (FR)

(72) Inventors: Marian M. Georges, East Brunswick, NJ (US); Sarah Kathryn Yuro, Jackson, NJ (US); Gracemarie Rose Papaleo, Helmetta, NJ (US); Santana Symczak, Howell, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/387,575

(22) Filed: Jul. 28, 2021

(65) Prior Publication Data

US 2023/0032376 A1 Feb. 2, 2023

(51) Int. Cl.
| | |
|---|---|
| *A61K 8/06* | (2006.01) |
| *A61K 8/04* | (2006.01) |
| *A61K 8/19* | (2006.01) |
| *A61K 8/26* | (2006.01) |
| *A61K 8/34* | (2006.01) |
| *A61K 8/49* | (2006.01) |
| *A61K 8/89* | (2006.01) |
| *A61K 8/891* | (2006.01) |
| *A61K 8/895* | (2006.01) |
| *A61Q 17/04* | (2006.01) |

(52) U.S. Cl.
CPC ............. *A61K 8/064* (2013.01); *A61K 8/042* (2013.01); *A61K 8/26* (2013.01); *A61K 8/345* (2013.01); *A61K 8/4926* (2013.01); *A61K 8/89* (2013.01); *A61K 8/895* (2013.01); *A61Q 17/04* (2013.01); *A61K 2800/30* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 5,166,355 A | 11/1992 | Leistner et al. | |
| 5,236,986 A | 8/1993 | Sakuta | |
| 5,237,071 A | 8/1993 | Leistner et al. | |
| 5,412,004 A | 5/1995 | Tachibana et al. | |
| 5,601,811 A | 2/1997 | Gallagher et al. | |
| 5,811,487 A | 9/1998 | Schulz et al. | |
| 5,837,793 A | 11/1998 | Harashima et al. | |
| 8,586,013 B2 | 11/2013 | Bradshaw et al. | |
| 9,320,689 B2 | 4/2016 | Cassin et al. | |
| 9,649,263 B2 | 5/2017 | Youssef et al. | |
| 9,655,825 B2 | 5/2017 | Youssef et al. | |
| 2005/0249690 A1* | 11/2005 | Rojas-Wahl | A61K 8/891 424/70.12 |
| 2006/0034875 A1 | 2/2006 | Nakanishi et al. | |
| 2006/0292096 A1 | 12/2006 | Yu | |
| 2007/0093619 A1 | 4/2007 | Bui et al. | |
| 2011/0033400 A1 | 2/2011 | Ehlis et al. | |
| 2012/0189676 A1 | 7/2012 | Susak et al. | |
| 2012/0301415 A1 | 11/2012 | Bui et al. | |
| 2016/0175205 A1* | 6/2016 | Debeaud | A61K 8/31 424/78.03 |
| 2016/0367470 A1* | 12/2016 | Chiou | A61K 8/064 |
| 2020/0085723 A1 | 3/2020 | Valverde et al. | |

FOREIGN PATENT DOCUMENTS

| | | |
|---|---|---|
| DE | 19726184 A1 | 12/1998 |
| EP | 893119 B1 | 9/2003 |
| EP | 1990372 A2 | 11/2008 |
| GB | 2303549 A | 2/1997 |
| WO | 2004/024798 A1 | 3/2004 |
| WO | 2018112679 A1 | 6/2018 |

OTHER PUBLICATIONS

French Search Report issued May 2, 2022 in French Patent No. 2108923, pp. 1-2.
Velvet matte Skin Tint Broad, Mintel GNPD, Record ID 3769885, p. 1-10 Published Mar. 2016.
Brinker CJ., and Scherer G.W., the physics and chemistry of sol-gel processing, Sol-Gel Science, pp. 1-12: Academic Press, 1990, New York, USA.

\* cited by examiner

*Primary Examiner* — Brian Gulledge
(74) *Attorney, Agent, or Firm* — Womble Bond Dickinson (US) LLP

(57) ABSTRACT

Water-in-oil sunscreen emulsion compositions including an aqueous phase emulsified within an external fatty phase are provided. The external fatty phase includes at least one silicone fatty compound and at least about 10% by weight of organic UV filters with respect to the entire sunscreen composition. The compositions include an emulsifying silicone elastomer and a non-elastomeric silicone surfactant. The compositions further include swellable clay and pigment.

23 Claims, No Drawings

SUNSCREEN EMULSION COMPRISING SILICONE EMULSIFIER BLEND

FIELD OF THE INVENTION

The present invention relates to cosmetic compositions and in particular, sunscreen emulsions including a blend of silicone emulsifiers.

DISCUSSION OF THE BACKGROUND

Cosmetic compositions with pigments in order to provide hiding power and color, such as those suitable for face make-up, are known. Cosmetic compositions including various emulsifiers are also known. However, compositions with both pigments and high levels of organic UV filters are difficult to formulate. The inventors have recognized that one problem with formulating such compositions is that incorporating relatively high levels of pigments and high levels of organic UV filters is that the levels of pigments and organic UV filters needed to provide various benefits to the user contribute to the composition's instability.

Accordingly, certain aspects of the present invention relate to compositions that are stable and have a pleasant aesthetic, can provide sun protection and can also provide color (tint), hiding power, and/or other benefits.

SUMMARY OF THE INVENTION

According to one aspect of the invention, the present invention relates to water-in-oil sunscreen emulsion compositions that include an aqueous phase emulsified within an external fatty phase. The external fatty phase includes at least about 10% by weight of organic UV filters with respect to the entire composition. The external fatty phase also includes at least one silicone fatty material. The composition further includes an emulsifying silicone elastomer and a non-elastomeric silicone surfactant. The composition further includes a swellable clay and a pigment.

According to another aspect of the invention, the present invention relates to methods of treating the skin. The method includes applying to said skin a water-in-oil sunscreen emulsion compositions that includes an aqueous phase emulsified within an external fatty phase. The external fatty phase includes at least about 10% by weight of organic UV filters with respect to the entire composition. The external fatty phase also includes at least one silicone fatty material. The composition further includes an emulsifying silicone elastomer and a non-elastomeric silicone surfactant. The composition further includes a swellable clay and a pigment.

In some embodiments it is desirable that the one or more organic UV-filter(s) either is selected from the group of, includes or consists of: homosalate, ethylhexyl salicylate and octocrylene.

In other embodiments, the composition is substantially free of one or more or all of avobenzone, oxybenzone, octylmethyoxycinnamate, inorganic sunscreens and volatile silicone oils.

It is to be understood that both the foregoing general description and the following detailed description are exemplary and explanatory only and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Actives basis" as used herein means considering only the particular component of ingredient (e.g., in a composition) and ignoring other chemically unrelated components that may be also be present in the same raw material source of that particular component. "Solids basis" as used herein means considering only components (e.g., in a composition) that are solid at room temperature and ignoring portions of the composition that are liquid, e.g., water and volatile solvents.

"Film former" or "film forming agent" as used herein means any material such as, for example, a polymer or a resin that leaves a film on the substrate to which it is applied.

"Polymer" as used herein means a compound which is made up of at least two monomers.

"Keratinous materials" includes materials containing keratin such as hair, skin, eyebrows, lips and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Furthermore, notably the range description "from about 1%, 2% or 3% to about 5%, 10% or 15%," includes at least 1%-5%, 1%-10%, 1%-15%, 2%-5%, 2%-10%, 2%-15%, 3%-5%, 3%-10%, and 3%-15%.

All percentages of ingredients herein are listed on an actives basis and on a weight basis unless specifically stated otherwise.

The term "substantially free" or "essentially free" as used herein means that there is less than about 2% by weight of a specific material added to a composition, based on the total weight of the compositions and may include less than about 1 wt. %, less than about 0.5 wt. %, less than about 0.1 wt. %, or none of the specified material. "Anhydrous" refers to substantially free of water.

The compositions of the present invention may be of various consistencies including, for example fluid, paste, semi-solid, and the like.

The compositions and methods of the present invention can comprise, consist of, or consist essentially of the essential elements and limitations of the invention described herein, as well as any additional or optional ingredients, components, or limitations described herein or otherwise useful in personal care.

Aqueous Phase

The composition of the invention includes an aqueous phase. The aqueous phase includes water and optionally other ingredients dissolved dispersed or suspended therein. Sufficient water may be present in the aqueous phase such that the concentration of water in the compositions as a whole is, for example less than about 40% by weight, such as from about 5% or 10% or 15% to about 30% or 35% or 40%. The aqueous phase may include preservatives, electrolytes such as sodium salts, various polyhydric alcohols, water-soluble UV filters, chelating agents, as well as various actives ingredients, vitamins, extracts and the like.

According to certain embodiments, the aqueous phase includes polyhydric alcohols such as glycerin, propanediol, hexylene glycol, butylene glycol and the like. The concentration of such polyhydric alcohols may be from about 5%, 7%, 10% to about 12% 15% or 20% by weight.

According to certain embodiments, the aqueous phase includes a skin lightening agent such as niacinamide. The concentration of such skin lightening agent in the composition may be from about 0.25%, 0.5% or 1% to about 1% or 2% or 5% by weight.

According to certain embodiments, the composition (e.g., the aqueous phase thereof) is substantially free of water-soluble UV filters such as various salts and their water-soluble derivatives of terephthalylidene dicamphor sulfonic acid, phenylbenzimidazole sulfonic acid, benzophenone-4, aminobenzoic acid (PABA), 4-Bis(polyethoxy)-para-aminobenzoic acid polyethoxyethyl ester (PEG-25 PABA), camphor benzalkonium methosulfate, methylene bis-benzotriazolyl tetramethylbutylphenol (Bisoctrizole), disodium phenyl dibenzimidazole tetrasulfonate (Bisdisulizole disodium), and tris-biphenyl triazine; their derivatives and corresponding salts; naphthalene bisimide derivatives and cinnamido amine cationic quaternary salts.

The aqueous phase is emulsified within an external fatty phase.

In certain notable embodiments, the composition is a water-in-oil (W/O) emulsion where the "O" represents a fatty phase including organic UV filters and at least one silicone fatty material. In certain other embodiments, the composition is a double emulsion (O/W/O emulsion). One skilled in the art will readily recognize that an "emulsified" and "emulsion" relate to a fine dispersion of droplets of, in this case of a discontinuous aqueous phase within a continuous oil phase. The emulsion is stabilized using emulsifiers.

Although the relative proportions of the aqueous phase and the fatty phase may vary, according to certain embodiments of the invention the fatty phase is present in a total concentration by weight that is greater than the aqueous phase emulsified therein.

External Fatty Phase

The external fatty phase includes one or more fatty materials, e.g., those compounds having a hydrophobic moiety and, in certain notable embodiments which are not amphiphilic and, as such, in this embodiment do not also include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the fatty material does not include hydroxyl moieties.

The external fatty phase includes one or more organic UV filters and at least one silicone fatty material and may also optionally include other ingredients dissolved dispersed or suspended therein.

Organic UV Filters

Organic UV (ultraviolet) filters are organic compounds that reduce UV radiation such as primarily by absorbing ultraviolet radiation. According to certain embodiments the at least one UV filter includes at least one salicylate compound and at least one β,β-Diphenylacrylate compound.

Mention may be made, as examples of the organic UV-filter(s), of those denoted below under their INCI names, and mixtures thereof.

Examples of particularly suitable salicylic compounds include Homosalate (homomentyl salicylate), such as marketed under the trademark "Eusolex HMS" by Rona/EM Industries; and ethylhexyl salicylate, such as marketed under the trademark "Neo Heliopan OS" by Haarmann and Reimer; glycol salicylate. Other examples of salicylate compounds include phenyl salicylate; dipropyleneglycol salicylate, such as marketed under the trademark "Dipsal" by Scher; and TEA salicylate, such as marketed under the trademark "Neo Heliopan TS" by Haarmann and Reimer.

Examples of particularly suitable β,β-Diphenylacrylate compounds include Octocrylene, such as marketed in particular under the trademark "Uvinul N539" by BASF; and Etocrylene, such as marketed in particular under the trademark "Uvinul N35" by BASF.

While according to certain embodiments, the one or more UV filters include only includes at least one salicylate compound and at least one β,β-Diphenylacrylate compound, according to certain other embodiments, other UV filters are included. Other such examples include Anthranilic compounds, dibenzoylmethane compounds, Cinnamic compounds, Camphor compounds, Benzophenone compounds, Triazine compounds, Benzotriazole compounds, Benzalmalonate compounds, Imidazoline compounds, Para-aminobenzoic acid compounds, Methylene bis-(hydroxyphenylbenzotriazol) compounds, and Benzoxazole compounds.

Anthranilic compounds include menthyl anthranilates, such as marketed under the trademark "Neo Heliopan MA" by Haarmann and Reimer.

The dibenzoylmethane compounds include Butyl methoxydibenzoylmethane, such as marketed in particular under the trademark "Parsol 1789" by Hoffmann-La Roche; and isopropyl dibenzoylmethane.

Cinnamic compounds include Ethylhexyl methoxycinnamate, such as marketed in particular under the trademark "Parsol MCX" by Hoffmann-La Roche; isopropyl methoxycinnamate; isopropoxy methoxycinnamate; isoamyl methoxycinnamate, such as marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Camphor compounds include benzylidenecamphor derivatives: 3-benzylidene camphor, such as manufactured under the trademark "Mexoryl SD" by Chimex; 4-methylbenzylidene camphor, such as marketed under the trademark "Eusolex 6300" by Merck; benzylidene camphor sulfonic acid, such as manufactured under the trademark "Mexoryl SL" by Chimex; camphor benzalkonium methosulfate, such as manufactured under the trademark "Mexoryl SO" by Chimex; terephthalylidene dicamphor sulfonic acid, such as manufactured under the trademark "Mexoryl SX" by Chimex; and polyacrylamidomethyl benzylidene camphor, such as manufactured under the trademark "Mexoryl SW" by Chimex.

Benzophenone compounds include Benzophenone-1 (2,4-dihydroxybenzophenone), such as marketed under the trademark "Uvinul 400" by BASF; benzophenone-2 (Tetrahydroxybenzophenone), such as marketed under the trademark "Uvinul D50" by BASF; Benzophenone-3 (2-hydroxy-4-methoxybenzophenone) or oxybenzone, such as marketed under the trademark "Uvinul M40" by BASF; benzophenone-4 (hydroxymethoxy benzophonene sulfonic acid), such as marketed under the trademark "Uvinul MS40" by BASF; benzophenone-5 (Sodium hydroxymethoxy benzophenone Sulfonate); benzophenone-6 (dihydroxy dimethoxy benzophenone); such as marketed under the trademark "Helisorb 11" by Norquay; benzophenone-8, such as marketed under the trademark "Spectra-Sorb UV-24" by American Cyanamid; benzophenone-9 (Disodium dihydroxy dimethoxy benzophenonedisulfonate), such as marketed under the trademark "Uvinul DS-49" by BASF; and benzophenone-12, and n-hexyl 2-(4-diethylamino-2-hydroxybenzoyl)benzoate (such as UVINUL A+ by BASF).

Triazine compounds include Diethylhexyl butamido triazone, such as marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine, such as marketed under the trademark "TINOSORB S" by CIBA GEIGY, and ethylhexyl triazone, such as marketed under the trademark "UVTNUL T150" by BASF.

Benzotriazole compounds include phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds include Dineopentyl 4'-methoxybenzalmalonate, and polyorganosiloxane comprising benzalmalonate functional groups, such as polysilicone-15, such as marketed under the trademark "Parsol SLX" by Hoffmann-LaRoche. Benzimidazole compounds, in particular, phenylbenzimidazole derivatives: Phenylbenzimidazole sulfonic acid, such as marketed in particular under the trademark "Eusolex 232" by Merck, and disodium phenyl dibenzimidazole tetrasulfonate, such as marketed under the trademark "Neo Heliopan AP" by Haarmann and Reimer.

Imidazoline compounds include Ethylhexyl dimethoxybenzylidene dioxoimidazoline propionate. Bis-benzoazolyl compounds: The derivatives as described in EP-669,323 and U.S. Pat. No. 2,463,264.

Para-aminobenzoic acid compounds include PABA (p-aminobenzoic acid), ethyl PABA, Ethyl dihydroxypropyl PABA, pentyl dimethyl PABA, ethylhexyl dimethyl PABA, such as marketed in particular under the trademark "Escalol 507" by ISP, glyceryl PABA, and PEG-25 PABA, such as marketed under the trademark "Uvinul P25" by BASF.

Methylene bis-(hydroxyphenylbenzotriazol) compounds include 2,2'-methylenebis[6-(2H-benzotriazol-2-yl)-4-methyl-phenol], such as marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol], such as marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197, 26,184, and EP-893,119, and Drometrizole trisiloxane, such as marketed under the trademark "Silatrizole" by Rhodia Chimie or-"Mexoryl XL" by L'Oréal.

Benzoxazole compounds include 2,4-bis[5-1(dimethylpropyl)benzoxazol-2-yl-(4-phenyl)imino]-6-(2-ethylhexyl) imino-1,3,5-triazine, such as marketed under the trademark of Uvasorb K2A by Sigma 3V. Screening polymers and screening silicones: The silicones described in WO 93/04665. Dimers derived from a-alkylstyrene: The dimers described in DE-19855649. 4,4-Diarylbutadiene compounds: 1,1-dicarboxy(2,2'-dimethylpropyl)-4,4-diphenylbutadiene.

In some embodiments desirable that the one or more organic UV-filter(s) either is selected from the group of, includes or consists of: homosalate, ethylhexyl salicylate, and octocrylene.

In other embodiments, the composition is substantially free of one or more or all of avobenzone, oxybenzone, octylmethyoxy cinnamate and optionally also inorganic sunscreens, such as sunscreen grade titanium dioxide and zinc oxide, such as those inorganic sunscreens having primary particle sizes of less than about 75 nm.

The at least one organic UV filter is present in an amount such that with respect to the entire composition, the concentration by weight is at least about 10% by weight, such as at least about 15% by weight, such as from about 10%, 12%, 14%, 15% to about 20%, 22%, 15%, 30% or 40% by weight.

Silicone Fatty Materials

Compositions of the present invention include at least one silicone fatty material in the external fatty phase and, in particular, at least one silicone oil. As one skilled in the art will readily recognize, by "silicones" or "silicone fatty materials," it is meant fatty materials having at least one silicon atom that is directly bonded to (1) at least one oxygen atom and further directly bonded to (2) at least one carbon atom such as included in a methyl group or a carbon that is a part of an (alkyl, aryl, etc.) chain of carbon atoms. Such organic compounds of silicon are typically referred to as organosilicones. The silicone may include two or more organosiloxane units.

As used herein, by "silicone oil," it is meant silicone fatty materials having a melting point of less than about 30C and generally insoluble in water and may include two or more alkyl siloxy groups. The silicone oil may be volatile or non-volatile. Suitable examples of silicone oils include volatile silicone oils, such as those having a flash point from about 40° C. to about 100° C. The volatile silicone oil may be linear or cyclic, having a viscosity, at room temperature, of less than or equal to 6 cSt, and having from 2 to 7 silicon atoms, optionally substituted with alkyl or alkoxy groups of 1 to 10 carbon atoms. Examples of suitable volatile silicone oils include, octyltrimethicone, hexyltrimethicone, cyclopentasiloxane, cyclohexasiloxane, polydimethylsiloxanes. While in certain embodiments, the compositions of the invention include volatile silicone oils, in other embodiments, the compositions are substantially free of these materials.

Non-volatile silicone oils include polymethylsiloxanes (PDMS) with a linear or cyclic silicone chain, which are liquid or pasty at room temperature, especially caprylyl methicone, cyclopolydimethylsiloxanes (cyclomethicones) such as phenyl trimethicones, cyclohexasiloxane; polydimethyl-siloxanes (CTFA designation "dimethicones") comprising alkyl or alkoxy groups, which are pendent or at the end of a silicone chain, these groups containing from 2 to 24 carbon atoms; polydiethyl siloxanes; and dimethicone fluids having viscosity from about 300 cPs at 25° C. to about 1500 cPs at 25° C. Particularly useful dimethicone fluids have viscosity from about 350 cPs at 25° C. to about 1000 cPs at 25° C. According to certain embodiments, the compositions are substantially free of volatile silicone oils.

According to certain embodiments the concentration of the at least one silicone fatty material in the composition as whole is from about 1%, 2%, or 3% or 5% or to about 5%, 8% 10% or 20% by weight, including all ranges and sub-ranges therebetween.

Other fatty materials that may be present in the fatty phase include fatty materials that may not be organic UV filters or silicone fatty materials. For example those materials having a carbon chain of at least six carbons in which none of the six carbons is a carbonyl carbon or has a hydrophilic moiety bonded directly to it or have two or more oxypropylene groups in sequence. The hydrophobic moiety may include linear, cyclic, aromatic, saturated or unsaturated groups.

Suitable examples of such compounds include oils such as vegetable oils (glyceryl esters of fatty acids, triglycerides) and fatty esters. Specific non-limiting examples include, without limitation, esters such as isopropyl palmitate, hexyl laurate, isohexadecane, isopropyl myristate, isononyl isononanoate $C_{12}$-$C_{15}$ alkyl benzoates, caprylic/capric triglycerides, pentaerythritol tetraoctanoate, and mineral oil and the like.

According to certain other embodiments, the fatty phase may include one or more waxes. By wax, it is meant a lipophilic fatty compound that is solid at room temperature (about 25° C.) and atmospheric pressure (760 mm Hg, i.e., 105 Pa), which undergoes a reversible solid/liquid change of state and which has a melting point of greater than 30° C., and in some embodiments, greater than about 55° C. up to about 120° C. or even as high as about 200° C. The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes. Silicone waxes may also be included.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

According to certain embodiments, the external fatty phase is characterized by a majority fraction of non-silicone fatty materials (also referred to herein as "non-silicones") which includes organic UV filters that are free of silicone moieties as well as hydrocarbons, fatty acid esters, or other fatty materials or compounds that do not include any silicone moieties; and a minority fraction of silicone fatty materials. By "majority fraction of non-silicones," or "minority fraction of silicone fatty materials," it is meant that in the sunscreen composition or in the external fatty phase the total weight percentage of non-silicone fatty materials is greater than the weight percentage of the one or more non-silicone fatty materials.

Silicone Resins

According to certain embodiments, other silicones that may be included in the fatty phase include silicone resins such as those selected from the group consisting of siloxysilicate resins, silsesquioxane resins, and silicone elastomers such as dimethicone/vinyl dimethicone crosspolymers.

In one embodiment, the silicone resins include those selected from a siloxysilicate resin, a silsequioxane resin, and combinations thereof. One non-limiting example of a siloxysilicate in accordance with the present invention is trimethylsiloxysilicate, which may be represented by the following formula:

[(CH3)3SiO]x(SiO4/2)y wherein x and y may, for example, range from 50 to 80. Such siloxysilicates are commercially available from General Electric, Dow Corning, Wacker, Milliken, Siltech, Grant Industries, Momentive and Shin-Etsu Silicones under the tradename Resin MQ®.

According to another embodiment of this invention, the compositions may contain silsesquioxane resins, including comprise at least one polypropyl silsesquioxane film forming resin.

Silsesquioxane resins are a specific form of silicone resin. Silicone resin nomenclature is known in the art as "MDTQ" nomenclature, whereby a silicone resin is described according to the various monomeric siloxane units which make up the polymer. Each letter of "MDTQ" denotes a different type of unit. When the film forming resin is made up predominantly of tri-functional units (or T units), it is generally called a silsesquioxane resin, which is described, for example in US 2006/0292096, herein incorporated by reference.

Examples of silsesquioxane resins that may be used in the present invention are alkyl silsesquioxane resins that are silsesquioxane homopolymers and/or copolymers having an average siloxane unit of the general formula R1n SiO(4-n)/2, wherein each R1 is a propyl group, wherein more than 80 mole % of R1 represent a C3-C10 alkyl group, n is a value of from 1.0 to 1.4, and more than 60 mole % of the copolymer comprises R1SiO3/2 units. As each R1 is a propyl group these polymers are called polypropylsilsesquioxane resins or "t-propyl" silsesquioxane resins. These resins and methods of making them are described, for example in U.S. Pat. No. 8,586,013, 2012/0301415, 2007/0093619, and 2006/0292096, all of which are herein incorporated by reference.

A non-limiting example of a polypropylsilsesquioxane resin suitable for use in the present invention is commercially available from Dow Corning as Dow Corning 670 Fluid or Dow Corning 680 Fluid. These Dow Corning resins have a general formula of RnSiO(4-n)/2 wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises RSiO3/2 units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

According to certain embodiments the concentration of the at least one silicone resin in the composition as whole is from about 0.1%, 0.25%, or 0.5% to about 0.5%, 1% 2% or 5% by weight, including all ranges and sub-ranges therebetween.

Pigment

Compositions of the present invention include pigment useful for providing color and/or opacity or hiding power. Suitable "color pigments" useful for providing makeup color are those having a color component other than white such as, for example, iron oxide particulates that may or have not have a surface treatment. The iron oxide particulates provide hiding powder to aid in concealing skin imperfections while imparting some additional visible color. Any of various cosmetic grades of iron oxide particulate are suitable for use in compositions of the present invention. In certain embodiments the iron oxide particulate has an average particle size in a range from about 0.1 micron to about 10 microns, such as from about 0.15 micron to about 1 microns. Notable iron oxides include red, black and brown iron oxides having a primary particle size less than one micron and surface treated with an organosilane, such as triethoxycaprylyl silane. Suitable examples include SunPURO® Iron Oxides available from Sun Chemical of Parsippany, New Jersey Other color pigments may also be included such as any of various other inorganic oxides that impart color such as chromium oxide. Other suitable color pigments include various inorganic lake pigments. According to other embodiments the pigment may be rather than a color pigment, an opacifying agent pigments such as a pigmentary grade of titanium dioxide, such as one having an average primary particle size greater than about 75 nanometers such as greater than about 200 nanometers, such as from about 200 to about 300 nanometers. According to other embodiments opacifying agent pigments such as mica, talc, or fluorphlogopite are included.

The concentration of pigments in the composition may range from about 2%, 3%, 4% 5% or 7% to about 7%, 8%, 10% or 15% by weight, including all ranges and subranges therebetween. In certain embodiments, the concentration of pigment is at least about 5% by weight.

Silicone Emulsifiers

The composition further includes two different classes (i.e., a "blend") of silicone emulsifiers (surfactants) in order to enhance the stability of the high loading of organic UV filters as well as the silicone oil and/or to providing wetting or dispersing of the particulate portion.

The first class of emulsifier that is included is an emulsifying silicone elastomer. The term "emulsifying silicone elastomer" is intended to mean a silicone elastomer comprising at least one hydrophilic chain.

The emulsifying silicone elastomer may be chosen from polyoxyalkylenated silicone elastomers and polyglycerolated silicone elastomers, and mixtures thereof.

The polyoxyalkylenated silicone elastomer is a crosslinked organopolysiloxane that can be obtained by crosslinking addition reaction of diorganopolysiloxane containing at least one hydrogen bonded to silicon and of a polyoxyalkylene having at least two ethylenically unsaturated groups.

Preferably, the polyoxyalkylenated crosslinked organopolysiloxane is obtained by crosslinking addition reaction (A1) of diorganopolysiloxane containing at least two hydrogens each bonded to a silicon, and (B1) of polyoxyalkylene containing at least two ethylenically unsaturated groups, in particular in the presence (C1) of a platinum catalyst, as described, for example, in U.S. Pat. Nos. 5,236,986 and 5,412,004.

In particular, the organopolysiloxane can be obtained by reaction of polyoxyalkylene (in particular polyoxyethylene and/or polyoxypropylene) containing dimethylvinylsiloxy end groups and of methylhydrogeno-polysiloxane containing trimethylsiloxy end groups, in the presence of a platinum catalyst.

The organic groups bonded to silicon atoms of the compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenyl-ethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, copolymers of dimethylsiloxane-methylhydrogenosiloxane containing trimethylsiloxy end groups, cyclic dimethylsiloxane-methylhydrogenosiloxane copolymers, and copolymers of dimethylsiloxane-methylhydrogenosiloxane-laurylmethylsiloxane containing trimethylsiloxy end groups.

Compound (C1) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated silicone elastomers may be formed from divinyl compounds, in particular polyoxyalkylenes having at least two vinyl groups, reacting with Si—H bonds of a polysiloxane.

The polyoxyalkylenated silicone elastomer according to the invention is preferably mixed with at least one hydrocarbon-based oil and/or one silicone oil so as to form a gel. In these gels, the polyoxyalkylenated elastomer can be in the form of non-spherical particles.

Polyoxyalkylenated elastomers are in particular described in U.S. Pat. Nos. 5,236,986, 5,412,004, 5,837,793 and 5,811,487.

Polyoxyalkylenated silicone elastomers that may be used include those sold under the names KSG-21, KSG-20, KSG-30, KSG-31, KSG-32, KSG-33, KSG-210, KSG-310, KSG-320, KSG-330, KSG-340 and X-226146 by the company Shin-Etsu, and DC9010 and DC9011 by the company Dow Corning, KSG-210 is particularly notable.

In another embodiment, the emulsifying silicone elastomer may also be chosen from polyglycerolated silicone elastomers.

The polyglycerolated silicone elastomer is a crosslinked elastomeric organopolysiloxane that can be obtained by a crosslinking addition reaction of diorganopolysiloxane containing at least one hydrogen bonded to silicon and of polyglycerolated compounds having ethylenically unsaturated groups, in particular in the presence of a platinum catalyst.

Preferably, the crosslinked elastomeric organopolysiloxane is obtained by crosslinking addition reaction (A) of diorganopolysiloxane containing at least two hydrogens each bonded to a silicon, and (B) of glycerolated compounds having at least two ethylenically unsaturated groups, in particular in the presence (C) of a platinum catalyst.

In particular, the organopolysiloxane can be obtained by reaction of a polyglycerolated compound containing dimethylvinylsiloxy end groups and of methylhydrogenopolysiloxane containing trimethylsiloxy end groups, in the presence of a platinum catalyst.

The organic groups bonded to the silicon atoms of compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. Preferably, said organic group is chosen from methyl, phenyl and lauryl groups.

Compound (A) can thus be chosen from methylhydrogenopolysiloxanes containing trimethylsiloxy end groups, copolymers of dimethylsiloxane-methyl-hydrogenosiloxane containing trimethylsiloxy end groups, dimethylsiloxane-methylhydrogenosiloxane cyclic copolymers, and copolymers of dimethylsiloxane-methyl-hydrogenosiloxane-laurylmethylsiloxane containing trimethylsiloxy end groups.

Compound (B) may be a polyglycerolated compound corresponding to formula (B') below:

in which m is an integer ranging from 2 to 6, n is an integer ranging from 2 to 200, preferably ranging from 2 to 100, preferably ranging from 2 to 50, preferably n ranging from 2 to 20, preferably from 2 to 10, and preferentially ranging from 2 to 5, and in particular equal to 3; Gly denotes:

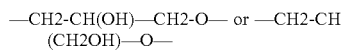

Advantageously, the sum of the number of ethylenic groups per molecule of compound (B) and of the number of hydrogen atoms bonded to silicon atoms per molecule of compound (A) is at least 4.

Compound (C) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black, or platinum on a support.

The polyglycerolated silicone elastomer according to the invention is generally mixed with at least one hydrocarbon-based oil and/or one silicone oil so as to form a gel. In these gels, the polyglycerolated elastomer is often in the form of non-spherical particles.

Such elastomers are in particular described in patent application WO 2004/024798.

As polyglycerolated silicone elastomers, mention may be made of those sold under the names KSG-710, KSG-810, KSG-820, KSG-830 and KSG-840 by the company Shin-Etsu.

The second class of emulsifier that is included in compositions of the invention is a non-elastomeric (e.g., non-crosslinked) silicone surfactant.

The non-elastomeric silicone surfactant may be any silicone surfactant that is not an emulsifying silicone elastomer, described above. Examples of non-elastomeric silicone surfactant include alkoxylated silicone surfactants. Examples include organosilicone compounds having alkoxylated allyl groups of any number of varying repeat units of ethylene oxide or propylene oxide. The alkoxylated group may in a terminal position and/or in a non-terminal position in the molecule.

According to one embodiment, the non-elastomeric silicone surfactant includes a non-terminal hydrophobic group. One suitable example is a copolymer of an alkoxylated dimethicone and a alkyl dimethicone such as a cetyl dimethicone copolyol such as INCI: Cetyl PEG/PPG-10/Dimethicone, available as ABIL EM-90 or ABIL EM-180 from Evonik.

The total concentration of the emulsifiers and/or surfactants in the composition may range from about 1%, 2% or 3% by weight to about 4%, 5%, 6% or 10% by weight, including all combinations of such ranges, relative to the total weight of the composition.

According to certain embodiments, the concentration by weight of the emulsifying silicone elastomer is no more than the concentration by weight of the non-elastomeric silicone surfactant. The concentration of the emulsifying silicone elastomer individually may range from about 0.2%, 0.4% or 0.75% to about 0.75%, 1% or 3%. The concentration of the non-elastomeric silicone surfactant individually may range from about 0.5%, 1% or 2% to about 2%, 3%, 5% or 10%. The concentration by weight ratio of the non-elastomeric silicone surfactant to the emulsifying silicone elastomer may range from about 0.5:1, 0.75:1 or 1:1 1.5:1 or 2:1 to about 2:1, 3:1 or 5:1.

Rheology Modifiers

Compositions of the present invention include a rheology modifier and, in particular a swellable clay. By "swellable clay" it is meant a clay material that is capable of swelling in water. An example of a swellable clay are smectite clays. The crystal structure of the smectite group, is an octahedral alumina sheet between two tetrahedral silica sheets. In one notable embodiment, the swellable clay is bentonite. Bentonite is a rock formed of highly colloidal and plastic clays composed mainly of montmorillonite, a clay mineral of the smectite group, and is produced by in situ devitrification of volcanic ash. In addition to montmorillonite, bentonite may contain feldspar, cristobalite, and crystalline quartz. Bentonite has an ability to form thixotrophic gels with water, an ability to absorb large quantities of water. Variations in interstitial water and exchangeable cations in the interlayer space affect the properties of bentonite and thus the commercial uses of the different types of bentonite.

One notable swellable clay suitable for use in the composition is BENTONE 38 VCG, commercially available from Elementis Specialties, East Windsor, New Jersey BENTONE GEL GTCC V is a an organically (disterammonium) modified hectorite.

The swellable clay may be present in the compositions of the present invention in an amount ranging from about 0.1%, 0.25%, or 0.5% by weight to about 0.5%, 0.75%%, 1% or 3%, based on the total weight of the composition, including all ranges and subranges within these ranges. Propylene carbonate, if present, may be present in the compositions of the present invention in an amount such that the ratio by weight of swellable clay to propylene carbonate is about 2:1 to about 5:1.

Compositions of the present invention include other rheology modifiers such as a hydrophobically modified silica such as a silica aerogel.

Silica aerogels are porous materials obtained by replacing (by drying) the liquid component of a silica gel with air. They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990. Silica aerogels, in general, have been disclosed in U.S. Pat. No. 9,320,689, the entire content of which is hereby incorporated by reference.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 m$^2$/g.

Mention may also be made of the aerogels sold by the company Cabot under the references AEROGEL TLD 201,

AEROGEL OGD 201, AEROGEL TLD 203, ENOVA® AEROGEL MT 1100, ENOVA AEROGEL MT 1200.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 m²/g.

The silica aerogel particles if used can be used in the inventive compositions from 0.1% to about 8% by weight, preferably from about 0.05%, 0.1%. or 0.15% to about 0.2%, 0.5%, 1% or 2% by weight, all weights based on the weight of the composition as a whole.

Other Ingredients

Compositions of the present invention may optionally include other functional ingredients such as those that can be readily dissolved, dispersed or suspended in the composition. These may include other particulate materials (organic, silicone-based); polymers such as for thickening/rheology modifying or film-forming; preservatives; solvents for the organic UV filters such as butyl octyl salicylate, dyes, fragrances; antioxidants; vitamins; humectants, and the like. A person skilled in the art will take care to select the optional additional additives and/or the amount thereof such that the advantageous properties of the composition according to the invention are not, or are not substantially, adversely affected by the envisaged addition.

According to certain embodiments, the composition is substantially free of various ingredients. As described above the compositions may be substantially free of one, more or all of: organic UV filters other than salicylates and β,β-Diphenylacrylate compounds (e.g., avobenzone, oxybenzone, octylmethoxy cinnamate), inorganic sunscreens, volatile silicone oils, non-silicone surfactants, and/or water-soluble UV filters.

The "water-soluble organic sunscreen ingredient" means any organic compound for screening out UV radiation, which can be fully dissolved in molecular form or miscible in a liquid aqueous phase or which can be dissolved in colloidal form (for example in micellar form) in a liquid aqueous phase.

Non-limiting examples of water-soluble organic sunscreen ingredients useful in the invention include, for example, terephthalylidene dicamphor sulfonic acid, phenylbenzimidazole sulfonic acid, benzophenone-4, aminobenzoic acid (PABA), 4-Bis(polyethoxy)-para-aminobenzoic acid polyethoxyethyl ester (PEG-25 PABA), camphor benzalkonium methosulfate, methylene bis-benzotriazolyl tetramethylbutylphenol (Bisoctrizole), disodium phenyl dibenzimidazole tetrasulfonate (Bisdisulizole disodium), and tris-biphenyl triazine; their derivatives and corresponding salts; naphthalene bisimide derivatives such as those described in European patent application EP1990372 A2, the entire contents of which is hereby incorporated by reference; and cinnamido amine cationic quaternary salts and derivatives such as those described in U.S. Pat. No. 5,601,811, the entire contents of which is hereby incorporated by reference, and mixtures thereof.

These substances may be selected variously by the person skilled in the art in order to prepare a composition which has the desired properties, for example, consistency or texture.

The other ingredients may be present in the composition in concentrations up to about 20%, such as from about 0%, 2%, or 5% to about 10%, 15%, or 20%, including all ranges and subranges therebetween.

According to certain particular embodiments of the invention, the water-in-oil sunscreen emulsion composition includes an aqueous phase emulsified within an external fatty phase. The external fatty phase includes: (1) at least about 10% by weight of organic UV filters with respect to the entire composition; (2) at least one silicone in a concentration by weight that is less than the total concentration by weight of the UV filters; (3) an emulsifying silicone elastomer; (4) a non-elastomeric silicone surfactant in a concentration by weight that is greater than the concentration by weight of the emulsifying silicone elastomer; (5) a swellable clay; (6) a silica aerogel; and (7) from about 5% to about 15% color pigment. The water-in-oil sunscreen emulsion composition is substantially free of titanium dioxide sunscreen (titanium dioxide having an average primary particle size less than about 75 nanometers), zinc oxide and oxybenzone. The water-in-oil sunscreen emulsion composition may be further substantially free of one, more or all of: organic UV filters other than salicylates and β,β-Diphenylacrylate compounds (e.g., avobenzone, oxybenzone, octylmethoxy cinnamate), volatile silicone oils, non-silicone surfactants, and/or water-soluble UV filters.

According to preferred embodiments of the present invention, methods of protecting, caring for and/or making up a keratinous material by applying compositions of the present invention to the keratinous material in an amount sufficient to protect, treat, care for and/or make up the keratinous material are provided. According to yet other preferred embodiments, methods of enhancing the appearance of a keratinous material by applying compositions of the present invention to the keratinous material in an amount sufficient to enhance the appearance of the keratinous material are provided.

The compositions may be applied to the desired area as needed, preferably once daily, and then preferably allowed to dry before subjecting to contact such as with clothing or other objects.

Compositions of the present invention may be made using methods known in the art such as charging a main vessel with silicone fatty material, organic UV filters, silicone emulsifiers, swellable clay, pigments, optional silicone film former and silica aerogel and homogenizing to form an oil phase preparation. Separately an aqueous phase preparation is prepared by combining water, optional ingredients such as polyhydric alcohol, actives, chelating agents, preservatives and the like. The aqueous phase may be heated if needed and cooled to room temperature. The aqueous phase prep is added to the oil phase prep and emulsified under shear.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example A—Inventive Compositions

Compositions consistent with the ingredients and approximate concentrations by weight in Table 1, below were prepared and evaluated for phase stability. Inventive Example 1 is consistent with embodiments of the invention described herein. Comparative Example 1 is comparative. The concentrations were in certain cases rounded for simplicity.

TABLE 1

| FUNCTION/TYPE | INVENTIVE EXAMPLE 1 | COMPARATIVE EXAMPLE 1 |
|---|---|---|
| Organic UV Filters | 18% | 18% |
| Silicone fatty compounds (non-volatile) | 8% | 11% |
| Emulsifying silicone elastomer | 1.2% | 1.3% |
| Non-elastomeric silicone emulsifier | 3% | 1% |
| Swellable clay | 0.5% | 0 |
| Pigments | 10% | 10% |
| Niacinamide | 2% | 2% |
| Water | 35% | 37% |
| Polyhydric Alcohols | 14% | 16% |
| Silicone resin | 0.5% | 0% |
| Silica Aerogel | 0.15% | 0.1% |
| Other Ingredients (appx.) | 7% | 4% |

Inventive Example 1 and Comparative Example 1 are nearly identical in composition except that Inventive Example 1 had more non-elastomeric silicone emulsifier than emulsifying silicone elastomer. The inventive example also included swellable clay, and silicone resin. When evaluated for phase stability, Inventive Example 1 was observed to be phase stable. Comparative Example 1 showed phase immediately.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. accordingly, the description is not intended to limit the invention to the form disclosed herein. Also, it is intended to the appended claims to construed to include alternative embodiments.

What is claimed is:

1. A water-in-oil sunscreen emulsion composition, comprising:
   an aqueous phase emulsified within an external fatty phase, wherein the external fatty phase comprises at least one silicone fatty compound, and
   wherein the external fatty phase comprises further comprises:
   a sufficient amount of organic UV filters such that the organic UV filters are present in a concentration of at least about 10% by weight with respect to the entire sunscreen composition;
   an emulsifying silicone elastomer which is a polyoxyalkylenated silicone elastomer;
   a non-elastomeric silicone surfactant which is an alkoxylated silicone surfactant;
   a swellable clay; and
   a pigment,
   wherein a weight ratio of non-elastomeric silicone surfactant to emulsifying silicone elastomer is from 1.5:1 to about 5:1.

2. The water-in-oil sunscreen emulsion composition of claim 1, wherein the water-in-oil sunscreen emulsion composition is substantially free of titanium dioxide sunscreen, zinc oxide and oxybenzone.

3. The water-in-oil sunscreen emulsion composition of claim 1, wherein the oil phase is characterized by having a minority fraction of silicones.

4. The water-in-oil sunscreen emulsion composition of claim 1, wherein the weight ratio of non-elastomeric silicone surfactant to emulsifying silicone elastomer is from 1.5:1 to about 3:1.

5. The water-in-oil sunscreen emulsion composition of claim 1, wherein the water-in-oil sunscreen emulsion composition is substantially free of avobenzone.

6. The water-in-oil sunscreen emulsion composition of claim 1, wherein the composition is substantially free of volatile silicones.

7. The water-in-oil sunscreen emulsion composition of claim 1, wherein the composition comprises at least about 15% organic UV filters.

8. The water-in-oil sunscreen emulsion composition of claim 1, wherein the composition comprises at least about 5% of color pigment.

9. The water-in-oil sunscreen emulsion composition of claim 1, wherein the composition further comprises a silicone resin.

10. The water-in-oil sunscreen emulsion composition of claim 1, wherein the composition further comprises a silica aerogel.

11. The water-in-oil sunscreen emulsion composition of claim 1, wherein the composition further comprises niacinamide.

12. The water-in-oil sunscreen emulsion composition of claim 1, wherein the composition further comprises a polyhydric alcohol.

13. The water-in-oil sunscreen emulsion composition of claim 1, wherein the composition comprises less than about 40% by weight of water.

14. The water-in-oil sunscreen emulsion composition of claim 1, wherein emulsifying silicone elastomer is present in the composition in a concentration by weight that is from about 0.2% to about 3% with respect to the entire sunscreen composition, wherein non-elastomeric silicone surfactant is present in the composition in a concentration by weight that is from about 2% to about 10%, wherein swellable clay is present in the composition in a concentration by weight that is from about 0.1% to about 1%, and wherein pigment is present in the composition in a concentration by weight from about 2% to about 10%.

15. The water-in-oil sunscreen emulsion composition of claim 1, wherein the weight ratio of non-elastomeric silicone surfactant to emulsifying silicone elastomer is from about 2:1 to about 5:1.

16. The water-in-oil sunscreen emulsion composition of claim 1, wherein the weight ratio of non-elastomeric silicone surfactant to emulsifying silicone elastomer is from about 2:1 to about 3:1.

17. The water-in-oil sunscreen emulsion composition of claim 1, wherein the emulsifying silicone elastomer consists of polyoxyalkylenated silicone elastomer(s).

18. The water-in-oil sunscreen emulsion composition of claim 6, wherein the weight ratio of non-elastomeric silicone surfactant to emulsifying silicone elastomer is from about 2:1 to about 3:1.

19. The water-in-oil sunscreen emulsion composition of claim 6, wherein the emulsifying silicone elastomer consists of polyoxyalkylenated silicone elastomer(s).

20. The water-in-oil sunscreen emulsion composition of claim 17, wherein the weight ratio of non-elastomeric silicone surfactant to emulsifying silicone elastomer is from about 2:1 to about 3:1.

21. The water-in-oil sunscreen emulsion composition of claim 19, wherein the weight ratio of non-elastomeric silicone surfactant to emulsifying silicone elastomer is from about 2:1 to about 3:1.

22. The water-in-oil sunscreen emulsion composition of claim 1, wherein the non-elastomeric silicone surfactant comprises a non-terminal hydrophobic group.

23. A method of treating the skin comprising applying the composition of claim 1 to said skin.

* * * * *